United States Patent [19]

Meier et al.

[11] Patent Number: 4,929,610

[45] Date of Patent: May 29, 1990

[54] COMPOSITION WHICH CONTAIN HYDROXYLATED DERIVATIVES OF VITAMIN $D_3$

[75] Inventors: Werner Meier, Bottmingen, Switzerland; Walter A. Rambeck, Munich, Fed. Rep. of Germany; Harald Weiser, Hochwald, Switzerland; Hermann Zucker, Munich, Fed. Rep. of Germany

[73] Assignee: Hoffmann-La Roche Inc., Nutley, N.J.

[21] Appl. No.: 384,865

[22] Filed: Jul. 21, 1989

Related U.S. Application Data

[63] Continuation of Ser. No. 880,620, Jun. 25, 1986, abandoned.

[30] Foreign Application Priority Data

Jul. 1, 1985 [CH] Switzerland ............... 2798/85
Apr. 24, 1986 [CH] Switzerland ............... 1663/86

[51] Int. Cl.[5] .............. A01N 45/00; A61K 31/59
[52] U.S. Cl. ............................. 514/167; 514/168; 552/653
[58] Field of Search ................. 514/167, 168; 260/397.2

[56] References Cited

U.S. PATENT DOCUMENTS

| | | | |
|---|---|---|---|
| 4,225,596 | 9/1980 | DeLuca | 260/397.2 |
| 4,495,181 | 1/1985 | Norman et al. | 514/167 |
| 4,617,297 | 10/1986 | Boris et al. | 514/167 |

FOREIGN PATENT DOCUMENTS

| | | | |
|---|---|---|---|
| 0045516 | 3/1985 | Japan | 514/167 |
| 0738585 | 3/1976 | U.S.S.R. | 514/168 |

OTHER PUBLICATIONS

Endocrinology 117 (5) 2203–2210, 1985.
Kidney Internatl. 26 (4) 490, 1984.
J. Nutr. 113 (12) 2505–15, 1983.
Clinical Science (1983) 65, 429–436.
Proceedings of the Sixth Workshop on Vitamin D, Merano, Italy, Mar. 1985, Norman et al. (ed.), Berlin/-New York, 1985.
Biochem. Biophys. Res. Comm. 126 (1) 490–501, 1985.

*Primary Examiner*—Mary C. Lee
*Assistant Examiner*—Zinna Northington-Davis
*Attorney, Agent, or Firm*—George M. Gould; Bernard S. Leon; William G. Isgro

[57] ABSTRACT

Novel combination preparations containing 1α,25-dihydroxy vitamin $D_3$ or 1α-hydroxy vitamin $D_3$ and 1α,24,25(or 1α,25,26)-trihydroxy vitamin $D_3$ are described. These preparations are useful in the treatment of various disorders which are characterized by disturbances of the calcium and phosphate metabolism such as osteoporosis and can also be used in animal nutrition.

23 Claims, No Drawings

COMPOSITION WHICH CONTAIN HYDROXYLATED DERIVATIVES OF VITAMIN D₃

This application is a continuation of application Serial No. 06/880,620, filed June 25, 1986, abandoned.

BRIEF SUMMARY OF THE INVENTION

This invention is concerned with novel pharmaceutical preparations or compositions which contain hydroxylated derivatives of vitamin D as active substances. In particular, the invention is concerned with pharmaceutical preparations or compositions containing $1\alpha,25$-dihydroxy-vitamin $D_3$ ($1,25(OH)_2D_3$) in admixture with $1\alpha,24,25$-trihydroxy-vitamin $D_3$ ($1,24,25(OH)_3D_3$) or $1\alpha,25,26$-trihydroxy-vitamin $D_3$ ($1,25,26(OH)_3D_3$) or $25,26$-dihydroxy-vitamin $D_3$ ($25,26(OH)_2D_3$) or $1\alpha,24,25$-trihydroxy-vitamin $D_3$ and $24,25$-dihydroxy-vitamin $D_3$ ($24,25(OH)_2D_3$); or $1\alpha,25,26$-trihydroxy-vitamin $D_3$ and $25,26$-dihydroxy-vitamin $D_3$; and pharmaceutical preparations or compositions containing $1\alpha$-hydroxy-vitamin $D_3$($1(OH)D_3$) in admixture with $1\alpha,24,25$-trihydroxy-vitamin $D_3$ or $1\alpha,25,26$-trihydroxy-vitamin $D_3$; as well as usual inert pharmaceutical adjuvants or carrier materials.

Furthermore, the invention is concerned with feedstuffs and feedstuff additives which contain the above-mentioned active substance mixtures and with the use of these active substance mixtures for the manufacture of pharmaceutical preparations, feedstuffs and feedstuff additives.

The preparations in accordance with the invention are suitable for increasing the intestinal calcium transport, the calcium and phosphate level in the serum, as well as the deposition of these minerals in the bones. These preparations can accordingly be used for the treatment of illnesses which are characterized by metabolic calcium and phosphate deficiency conditions, especially those in which the concentration of endogenously-produced $1\alpha,25$-dihydroxy-vitamin $D_3$ lies below the normal value.

DETAILED DESCRIPTION OF THE INVENTION

The invention is concerned with novel pharmaceutical preparations or compositions which contain hydroxylated derivatives of vitamin D as active substances. In particular, the invention is concerned with pharmaceutical preparations or compositions containing $1\alpha,25$-dihydroxy-vitamin $D_3$ ($1,25(OH)_2D_3$) in admixture with $1\alpha,24,25$-trihydroxy-vitamin $D_3$ ($1,24,25(OH)_3D_3$) or $1\alpha,25,26$-trihydroxy-vitamin $D_3$ ($1,25,26(OH)_3D_3$) or $25,26$-dihydroxy-vitamin $D_3$ ($25,26(OH)_2D_3$) or $1\alpha,24,25$-trihydroxy-vitamin $D_3$ and $24,25$-dihydroxy-vitamin $D_3$ ($24,25(OH)_2D_3$); or $1\alpha,25,26$-trihydroxy-vitamin $D_3$ and $25,26$-dihydroxy-vitamin $D_3$; and pharmaceutical preparations or compositions containing $1\alpha$-hydroxy-vitamin $D_3$ ($1(OH)D_3$) in admixture with $1\alpha,24,25$-trihydroxy-vitamin $D_3$ or $1\alpha,25,26$-trihydroxy-vitamin $D_3$; as well as usual inert pharmaceutical adjuvants or carrier materials.

The invention accordingly embraces the following active substance combinations $1,25(OH)_2D_3 + 1,24,25(OH)_3D_3$ $1,25(OH)_2D_3 + 1,25,26(OH)_3D_3$ $1,25(OH)_2D_3 + 25,26(OH)_2D_3$ $1,25(OH)_2D_3 + 24,25(OH)_2D_3 + 1,24,25(OH)_3D_3$ $1,25(OH)_2D_3 + 25,26(OH)_2D_3 + 1,25,26(OH)_3D_3$ $1(OH)D_3 + 1,24,25(OH)_3D_3$ $1(OH)D_3 + 1,25,26(OH)_3D_3$.

Furthermore, the invention is concerned with feedstuffs and feedstuff additives which contain the above-mentioned active substance mixtures and with the use of these active substance mixtures for the manufacture of pharmaceutical preparations, feedstuffs and feedstuff additives.

It is known that hydroxylated vitamin D derivatives such as $1\alpha$-hydroxy-vitamin $D_3$, $1\alpha,25$-dihydroxy-vitamin $D_3$ and $1\alpha,24,25$-trihydroxy-vitamin $D_3$ can be used for the treatment of illnesses which are based on a deficiency of vitamin D or of its pharmacologically active metabolites. It has surprisingly been found that the administration of the active substance in accordance with the invention brings about therapeutic advantages compared with the administration of the individual substances. In a preferred embodiment the invention is concerned with pharmaceutical preparations containing $1,24,25(OH)_3D_3$ or $1,25,26(OH)_3D_3$ in admixture with $1,25(OH)_2D_3$. The combination of $1,24,25(OH)_3D_3$ with $1(OH)D_3$ is also preferred. $1\alpha,24,25$-Trihydroxy-vitamin $D_3$, preferably the 24R-epimer, and $1\alpha,25,26$-trihydroxy-vitamin $D_3$ intensify the activity of $1\alpha$-hydroxy-vitamin $D_3$ and $1\alpha,25$-dihydroxy-vitamin $D_3$ in concentrations in which they alone are much less active. This synergistic effect is preserved even in the case of disorders of $1\alpha$-hydroxylation in the kidneys. The calcium mobilization from the bones declines upon administering an active substance combination in accordance with the invention, while simultaneously the mineralization of the bones increases. By the combined administration of $1\alpha,24,25$(or $1\alpha,25,26$)-trihydroxy-vitamin $D_3$ with $1\alpha$-hydroxy- or $1\alpha,25$-dihydroxy-vitamin $D_3$ the last-named compounds can be administered in lower dosages than when they are administered alone, whereby toxic side effects are avoided or reduced. The relative proportions of the active substances in the preparations in accordance with the invention is not critical in a narrow range. Conveniently, the weight ratio of $1\alpha,24,25$-trihydroxy-vitamin $D_3$ to $1\alpha$-hydroxy- or $1\alpha,25$-dihydroxy-vitamin $D_3$ amounts to about 5:1 to about 1:5. A weight ratio of about 1:1 is preferred. The weight ratio of $1,25(OH)_2D_3$ to $1,25,26(OH)_3D_3$ can lie between 1:2 and 1:50, it is preferably 1:10. The weight ratio of $1,25(OH)_2D_3$ to $24,25(OH)_2D_3$ or $25,26(OH)_2D_3$ can amount to 1:2 to 1:20, it is preferably 1:10. The efficacy of the active substance combinations in accordance with the invention is evident from the test results when are presented hereinafter.

I. VITAMIN D TEST ON GROWING CHICKENS

(a) Curative Test

The preparations were administered to male chicks with the feed. In a pre-period the animals received a rachitogeneous vitamin D-free feed during 8 days. In the subsequent test period the animals received the same feed with the addition of the active substances for a period of 6 days. The bone analysis was carried out with the right tarsus (phalanges I and II of the middle toe). The dry weight of the bones was determined after boiling with water for 20 minutes, removing soft constituents, tendons and cartilage and drying at 100° C.

(b) Prophylactic Test

The test was carried out as described under (a), but the active substances were administered from the first day of life for a period of 21 days.

Calcium-binding protein (CaBP) was obtained from mucous membrane homogenates of the duodenum according to Corradino et al., Science 172, 731–3 (1971); the determination was carried out according to Wasserman et al. Science 152, 791–3 (1966) by adding $^{45}$Ca in the presence of a cation exchanger and determining the percentage of $^{45}$Ca present in the protein solution based on the total activity per mg of protein (specific activity of the CaBP). The activity of the alkaline phosphatase in the serum was determined according to Bergmeyer, Methoden der enzymatischen Analyze, Vol. 1, 3rd Edition, pp. 888–892.

The results of this test are compiled in Tables 1 to 3. The vitamin D activity shows itself in the increase in the CaBP activity and in the amount of bone ash and in the decrease in the alkaline phosphatase activity. The values ascertained show that an active substance combination in accordance with the invention exerts a more than additive activity compared with the individually administered components.

In a further series of tests with chicks the 1α-hydroxylase of the kidneys was inhibited according to Rambeck et al., Internat. J. Vit. Nutr. Res. 54, 25–34 (1984) by adding strontium to the feed. The test values given in Table 4 show that the synergistic effect of an active substance combination in accordance with the invention is observed even in the case of interfering kidney hydroxylation.

II. BONE CALCIUM MOBILIZATION IN CHICKENS

Chickens received a calcium-free diet during one week. Thereafter, the test substances were administered intravenously in 0.1 ml of 75% ethanol. 12 hours thereafter the Ca values in the serum were determined. The results presented in Table 5 show that the Ca mobilization from the bones upon administering an active substance combination in accordance with the invention is not greater than with the administration of the components alone.

III. QUAIL EGGSHELL TEST

This test determines the vitamin D activity on the basis of the Ca elimination of the animal by means of the eggshell. The test was carried out as described by Zucker et al., Naturwiss. 55, 447–455 (1968). The results presented in Table 6 likewise show a more than additive effect of an active substance combination in accordance with the invention.

IV. CURATIVE VITAMIN D TEST ON RATS

This test determines the vitamin D activity on the degree of calcification of the epiphysical cartilage of the tibia as described by Weiser in "Dar Tier im Experiment". Editor Wolf H. Weihe, Publisher Hans Huber, Bern-Stuttgart-Wien, 1978, 1,24(OH)$_2$D$_3$ or/and 1,24,25(OH)$_3$D$_3$ dissolved in ethanol/propylene glycol (1:10) was/were administered daily during 7 days with a probang to in each case 16 animals per group. One day later X-ray photographs were prepared and the calcification of the epiphysial cartilage was classified on the basis of the 12-point scale. A synergistic effect was achieved with an active substance combination in accordance with the invention in this test procedure (Table 7).

TABLE 1

Vitamin D test on growing chickens.
(a) Curative chick test, 11 animals/group
Combination of 1,25(OH)$_2$D$_3$ and 1,24,25(OH)$_3$D$_3$

| Addition to diet per kg | CaBP (specific activity) | % Bone ash of dried weight (pooled) | Alk. phosphatase (pooled) [units] |
|---|---|---|---|
| (Neg. control) | 1.87 ± 0.40 | 25.7 | 17 276 |
| 1.5 μg 1,25(OH)$_2$D$_3$ | 3.69 ± 1.58 | 28.8 | 14 788 |
| 1.5 μg 1,24,25(OH)$_3$D$_3$ | 1.75 ± 0.36 | 26.3 | 15 293 |
| 3.0 μg 1,24,25(OH)$_3$D$_3$ | 2.31 ± 0.40 | 26.7 | 15 360 |
| 1.5 μg 1,25(OH)$_2$D$_3$ + 1.5 μg 1,24,25(OH)$_3$D$_3$ | 6.39 ± 1.49 | 30.2 | — |
| 1.5 μg 1,25(OH)$_2$D$_3$ + 3.0 μg 1,24,25(OH)$_3$D$_3$ | 6.69 ± 1.27 | 31.0 | 11 293 |

TABLE 2

Vitamin D test on growing chickens
(b) Prophylactic test, 10 animals/group
Combination of 1,25(OH)$_2$D$_3$ and 25,26(OH)$_2$D$_3$ or 1,25,26(OH)$_3$D$_3$

| Addition to diet per kg | CaBP (specific activity) | % Bone ash of dry weight (pooled) | Alk. phosphatase (pooled) [units] | Ca in serum [mg/100 ml] | Weight gain [g] |
|---|---|---|---|---|---|
| (negative control) | 1.0 | 22.9 | 23 615 | 5.91 | 161 |
| 8 μg vitamin D$_3$ | 5.1 | 33.5 | 10 589 | 8.24 | 417 |
| 0.5 μg 1,25(OH$_2$)D$_3$ | 1.5 | 25.8 | 21 633 | 6.17 | 262 |
| 1.0 μg 1,25(OH)$_2$D$_3$ | 2.0 | 30.3 | 14 296 | 7.05 | 365 |
| 5 μg 1,25,26(OH)$_3$D$_3$ | 1.6 | 25.8 | 17 220 | 7.21 | 254 |
| 15 μg 1,25,26(OH)$_3$D$_3$ | 3.2 | 35.0 | 14 245 | 8.79 | 378 |
| 5 μg 25,26(OH)$_2$D$_3$ | 1.6 | 24.2 | 17 473 | 6.73 | 260 |
| 15 μg | 1.9 | 26.7 | 25 339 | 6.18 | 244 |

TABLE 2-continued

Vitamin D test on growing chickens
(b) Prophylactic test, 10 animals/group
Combination of $1,25(OH)_2D_3$ and $25,26(OH)_2D_3$ or $1,25,26(OH)_3D_3$

| Addition to diet per kg | CaBP (specific activity) | % Bone ash of dry weight (pooled) | Alk. phosphatase (pooled) [units] | Ca in serum [mg/100 ml] | Weight gain [g] |
|---|---|---|---|---|---|
| $25,26(OH)_2D_3$ 0.5 μg $1,25(OH)_2D_3$ + 5 μg $1,25,26(OH)_3D_3$ | 2.7 | 30.9 | 19 137 | 7.98 | 371 |
| 0.5 μg $1,25(OH)_2D_3$ + 5 μg $25,26(OH)_2D_3$ | 2.4 | 27.1 | 15 783 | 6.35 | 297 |
| 0.5 μg $1,25(OH)_2D_3$ + 15 μg $25,26(OH)_2D_3$ | 2.1 | 28.3 | 16 641 | 7.22 | 337 |
| 0.5 μg $1,25(OH)_2D_3$ + 15 μg $1,25,26(OH)_3D_3$ | 4.5 | 35.4 | 6 026 | 9.50 | 410 |

TABLE 3

Vitamin D test on growing chickens.
(Curative chick test), 11 animals/group
Combination of $1(OH)D_3$ and $1,24,25(OH)_3D_3$

| Addition to diet per kg | CaBP (specific activity) | % Bone ash of dry weight (pooled) |
|---|---|---|
| (Neg. control) | 1.43 ± 0.46 | 27.9 |
| 1.0 μg $1(OH)D_3$ | 1.50 ± 0.44 | 29.2 |
| 1.5 μg $1,24,25(OH)_3D_3$ | 1.68 ± 0.35 | 28.8 |
| 1.0 μg $1(OH)D_3$ + 1.5 μg $1,24,25(OH)_3D_3$ | 2.97 ± 0.75 | 31.0 |

TABLE 4

Vitamin D test on growing chickens
(Curative chick test) 1α-hydroxylation inhibited by strontium, 10 animals/group
Combination of $1,25(OH)_2D_3$ and $1,24,25(OH)_3D_3$

| Addition to diet per kg | CaBP (specific activity) | % Bone ash of dry weight (pooled) |
|---|---|---|
| (Neg. control) | 1.54 | 20.1 |
| 3 μg $1,25(OH)_2D_3$ | 3.31 | 21.2 |
| 3 μg $1,24,25(OH)_3D_3$ | 1.57 | 19.6 |
| 3 μg $1,25(OH)_2D_3$ + 3 μg $1,24,25(OH)_3D_3$ | 4.65 | 22.3 |

TABLE 5

Bone calcium mobilization in chickens.
(1 week calcium-free diet)

| i.v. dose | mg Ca/100 ml serum after 12 hours |
|---|---|
| (Neg. control) | 4.6 |
| 0.013 μg $1,25(OH)_2D_3$ | 4.8 |
| 0.025 μg $1,25(OH)_2D_3$ | 5.0 |
| 0.05 μg $1,25(OH)_2D_3$ | 5.3 |
| 0.125 μg $1,25(OH)_2D_3$ | 5.5 |
| 0.25 μg $1,25(OH)_2D_3$ | 5.9 |
| 1.25 μg $1,25(OH)_2D_3$ | 6.5 |
| 2.50 μg $1,25(OH)_2D_3$ | 7.4 |
| 0.05 μg $1,24,25(OH)_3D_3$ | 5.4 |
| 0.25 μg $1,24,25(OH)_3D_3$ | 5.7 |
| 1.25 μg $1,24,25(OH)_3D_3$ | 6.3 |
| 0.05 μg $1,24,25(OH)_3D_3$ + 0.25 μg $1,25(OH)_2D_3$ | 5.4 |
| 0.25 μg $1,24,25(OH)_3D_3$ + 0.25 μg $1,25(OH)_2D_3$ | 5.8 |
| 1.25 μg $1,24,25(OH)_3D_3$ + 0.25 μg $1,25(OH)_2D_3$ | 6.4 |

TABLE 6

Eggshell test on the Japanese quail
12 animals/group, combination of $1,25(OH)_2D_3$ and $1,24,25(OH)_2D_3$

| Addition to diet per kg | Eggshell dry weight in mg per animal and day |
|---|---|
| (Neg. control) | 56 |
| 2.0 μg vitamin $D_3$ | 87 |
| 3.5 μg vitamin $D_3$ | 309 |
| 5.0 μg vitamin $D_3$ | 563 |
| 0.27 μg $1,25(OH)_2D_3$ | 91 |
| 5.63 μg $1,24,25(OH)_3D_3$ | 126 |
| 0.27 μg $1,25(OH)_2D_3$ + 5.63 μg $1,24,25(OH)_3D_3$ | 271 |

TABLE 7

Curative vitamin D test on rats
(X-ray test), 16 animals/group
Combination of $1,25(OH)_2D_3$ and $1,24,25(OH)_3D_3$

| Dosage per animal and day | Calcification of the epiphysial cartilage (scoring-values ± SEM after 7 days) |
|---|---|
| Negative control | 0 |
| 0.0203 μg $1,25(OH)_2D_3$ | 4.4 ± 0.21 |
| 0.0105 μg $1,24,25(OH)_3D_3$ | 1.8 ± 0.21 |
| 0.0210 μg $1,24,25(OH)_3D_3$ | 3.7 ± 0.18 |
| 0.0203 μg $1,25(OH)_2D_3$ plus 0.0105 μg $1,24,25(OH)_3D_3$ | 7.8 ± 0.32 |
| 0.0203 μg $1,25(OH)_2D_3$ plus 0.0210 μg $1,24,25(OH)_3D_3$ | 9.8 ± 0.21 |

The preparations in accordance with the invention are suitable for increasing the intestinal calcium transport, the calcium and phosphate level in the serum, as well as the deposition of these minerals in the bones. These preparations can accordingly be used for the treatment of illnesses which are characterized by metabolic calcium and phosphate deficiency conditions, especially those in which the concentration of endogenously-produced 1α,25-dihydroxy-vitamin $D_3$ lies below the normal value. Treatment of illnesses characterized by metabolic calcium and phosphate deficiency conditions comprises administering an effective amount of a mixture of hydroxylated derivatives of vitamin D in accordance with the invention to a warm-blooded animal in need of such treatment. Examples of such illnesses are osteomalacia, osteoporosis, rachitis, osteitis fibrosa cystica, renal osteodystrophia, osteosclerosis, convulsions, osteopenia, fibrogenesis imperfecta ossium, secondary hyperparathyroidism, hypoparathyroidism, cirrhosis, obstructive jaundice, medullary carcinoma, chronic renal illnesses, hypophosphatamic vitamin D-resistant rachitis, vitamin D-dependent rachitis, sarcoidosis, glucocorticoid antagonism, misabsorption syndrome, steatorrhea, tropical sprue, idiopathic hypercalcaemia and milk fever. Furthermore, the preparations can be used e.g. as feed additives for the prevention of thin-shelled eggs, especially hen and turkey eggs, and for the treatment or prevention of bone black in poultry.

The preparations in accordance with the invention can be administered to humans in daily dosages of about 0.01–1, preferably 0.05–0.2, microgram in the case of the above-named illnesses. The preparations in accordance with the invention can be administered orally, subcutaneously, intramuscularly, intravenously, intraperitoneally or topically. Examples of pharmaceutical preparations are tablets, capsules or elixirs for oral administration and sterile solutions or suspensions for parenteral administration. These pharmaceutical preparations can contain the following adjuvants: binding agents such as gum tragacanth, acacia, maize starch or gelatin; excipients such as calcium phosphate; disintegrating agents such as maize starch, potato starch or alginic acid; glidants such as magnesium stearate, sweeteners such as sucrose, lactose or saccharin; flavoring agents such as peppermint, wintergreen or oil of sherry. Other materials such as coatings for modifying the appearance of the preparations can also be used. Tablets can be coated e.g. with shellac and/or sugar. A syrup or elixir can contain the active substances, sucrose as the sweetener, methylparaben and propylparaben as preserving agents, coloring substances and flavoring substances such as cherry or orange flavors.

For the treatment of milk fever in pregnant ruminants there come into consideration dosages of 0.05–1.5 mg/day, based on $1,25(OH)_2D_3$ or $1(OH)D_3$, in the usual forms of administration. In the case of administration to poultry there come into consideration dosages of 0.025–2.5 μg/kg feed, based on $1,25(OH)_2D_3$ or $1(OH)D_3$, or correspondingly adapted amounts in the drink.

Sterile preparations for injection and/or for topical administration can be manufactured in the usual manner by dissolving or suspending the active substances in a vehicle such as a 10–20% ethanol/water mixture, a 10–20% propylene glycol/water mixture, a naturally occurring vegetable oil such as sesame oil, groundnut oil, cottonseed oil; or a synthetic fatty binding agent such as ethyl oleate.

The following Examples illustrate the invention further.

EXAMPLE 1

The active substances can be dissolved in a pharmaceutically usable solvent such as alcohol, propylene glycol, glycerine or polyethylene glycol. Surface-active agents such as polyethylene glycol, sorbitan esters, dioctyl sodium sulphosuccinate, and/or polyoxyethylene-polyoxypropylene copolymers can be added for solubilization. A preserving agent can also be added to prevent microbial growth. Examples of capsule formulations which can be made up from such mixtures are:

| (a) | Per capsule |
|---|---|
| 1α,25-Dihydroxy-vitamin $D_3$ | 0.05–0.5 μg |
| 1α,24,25-Trihydroxy-vitamin $D_3$ | 0.05–0.5 μg |
| Polyethylene glycol (PEG) | 400.0 mg |
| Butylated hydroxyanisole (BHA) | 0.2 mg |
| Ascorbyl palmitate | 1.0 mg |

The active substances are added to a solution of BHA and ascorbyl palmitate in PEG and the mixture is dissolved under a nitrogen atmosphere. The liquid is filled into soft capsules.

| (b) | Per capsule |
|---|---|
| 1α,25-Dihydroxy-vitamin $D_3$ | 0.05–0.5 μg |
| 1α,24,25-Trihydroxy-vitamin $D_3$ | 0.05–0.5 μg |
| PEG 400 (or PEG 6000) | 200.0 mg |
| Polyoxyethylene sorbitan monoleate or monostearate (Polysorbate 80 or Polysorbate 60) | 200.0 mg |
| BHA | 0.2 mg |
| Ascorbyl palmitate | 1.0 mg |

The mixture of PEG 6000 and Polysorbate 60 is heated, then the BHA and the ascorbyl palmitate are added and finally the active substances are added under nitrogen. The mixture is filled into hard capsules.

| (c) | Per capsule |
|---|---|
| 1α,25-Dihydroxy-vitamin $D_3$ | 0.05–0.5 μg |
| 1α,25,26-Trihydroxy-vitamin $D_3$ | 0.5–5 μg |
| PEG 400 | 100.0 mg |
| PEG 4000 | 300.0 mg |
| BHA | 0.2 mg |
| Butylated hydroxytoluene (BHT) | 0.1 mg |
| Ascorbyl palmitate | 1.0 mg |

The mixture of PEG 400 and PEG 4000 is heated, then the BHT, BHA and the ascorbyl palmitate are added and finally the active substances are added and dissolved under nitrogen. The mixture is filled into hard capsules.

EXAMPLE 2

0.25–2.5 μg of 1α,25-dihydroxy-vitamin $D_3$ and 0.25–2.5 μg of 1α,24,25-trihydroxy-vitamin $D_3$ are admixed per kg of feed with a basic chicken feed manufactured according to standards for the feeding of poultry.

We claim:

1. A pharmaceutical composition wherein a pharmaceutical carrier is combined with a mixture of hydroxylated derivatives of vitamin D which mixtures are selected from the group consisting of the following mixtures: 1α,25-dihydroxy-vitamin $D_3$ and 1α,24,25-trihydroxy-vitamin $D_3$; $1\alpha,25$-dihydroxy-vitamin $D_3$ and $1\alpha,25,26$-trihydroxy-vitamin $D_3$; $1\alpha,25$-dihydroxy-vitamin $D_3$ and $25,26$-dihydroxy-vitamin $D_3$; $1\alpha,25$-dihydroxy-vitamin $D_3$, $24,25$-dihydroxy-vitamin $D_3$, and $1\alpha,24,25$-trihydroxy-vitamin $D_3$; $1\alpha,25$-dihydroxy-vitamin $D_3$, $25,26$-dihydroxy-vitamin $D_3$, and $1\alpha,25,26$-trihydroxy-vitamin $D_3$; $1\alpha$-hydroxy-vitamin $D_3$; and $1\alpha,24,25$-trihydroxy-vitamin $D_3$; and $1\alpha$-hydroxy-vitamin $D_3$ and $1\alpha,25,26$-trihydroxy-vitamin $D_3$; and a pharmaceutical carrier material.

2. A pharmaceutical composition in accordance with claim 1, wherein the mixture of hydroxylated derivatives of vitamin D is $1\alpha,25$-dihydroxy-vitamin $D_3$ and $1\alpha,25,26$-trihydroxy-vitamin $D_3$.

3. A pharmaceutical composition in accordance with claim 1, comprising a mixture of hydroxylated derivatives of vitamin D selected from the group consisting of the following mixtures $1\alpha,25$-dihydroxy-vitamin $D_3$ and $1\alpha,24,25$-trihydroxy-vitamin $D_3$; and $1\alpha$-hydroxy-vitamin $D_3$ and $1\alpha,24,25$-trihydroxy-vitamin $D_3$.

4. A pharmaceutical composition in accordance with claim 3, wherein the $1\alpha,24,25$-trihydroxy-vitamin $D_3$ is the 24R-epimer.

5. A pharmaceutical composition in accordance with claim 3, wherein the weight ratio of $1\alpha,25$-dihydroxy-vitamin $D_3$ or $1\alpha$-hydroxy-vitamin $D_3$ to $1\alpha,24,25$-trihydroxy-vitamin $D_3$ is about 5:1 to about 1:5.

6. A pharmaceutical composition in accordance with claim 5, wherein the weight ratio of $1\alpha,25$-dihydroxy-vitamin $D_3$ or $1\alpha$-hydroxy-vitamin $D_3$ to $1\alpha,24,25$-trihydroxy-vitamin $D_3$ is about 1:1.

7. A pharmaceutical composition in accordance with claim 1, comprising about 0.05 to about 0.5 μg of each hydroxylated derivative of vitamin D per dosage unit.

8. A feedstuff comprising a mixture of hydroxylated derivatives of vitamin D which mixture is selected from the group consisting of the following mixtures: $1\alpha,25$-dihydroxy-vitamin $D_3$ and $1\alpha,24,25$-trihydroxy-vitamin $D_3$; $1\alpha,25$-dihydroxy-vitamin $D_3$ and $1\alpha,25,26$-trihydroxy-vitamin $D_3$; $1\alpha,25$-dihydroxy-vitamin $D_3$ and $25,26$-dihydroxy-vitamin $D_3$; $1\alpha,25$-dihydroxy-vitamin $D_3$, $24,25$-dihydroxy-vitamin $D_3$, and $1\alpha,24,25$-trihydroxy-vitamin $D_3$; $1\alpha,25$-dihydroxy-vitamin $D_3$, $25,26$-dihydroxy-vitamin $D_3$, and $1\alpha,25,26$-trihydroxy-vitamin $D_3$; $1\alpha$-hydroxy-vitamin $D_3$; and $1\alpha,24,25$-trihydroxy-vitamin $D_3$; and $1\alpha$-hydroxy-vitamin $D_3$ and $1\alpha,25,26$-trihydroxy-vitamin $D_3$.

9. A feedstuff in accordance with claim 8, wherein the mixture of hydroxylated derivatives of vitamin D is $1\alpha,25$-dihydroxy-vitamin $D_3$ and $1\alpha,25,26$-trihydroxy-vitamin $D_3$.

10. A feedstuff in accordance with claim 8, comprising a mixture of hydroxylated derivatives of vitamin D selected from the group consisting of the following mixtures: $1\alpha,25$-dihydroxy-vitamin $D_3$ and $1\alpha,24,25$-trihydroxy-vitamin $D_3$; and $1\alpha$-hydroxy-vitamin $D_3$ and $1\alpha,24,25$-trihydroxy-vitamin $D_3$.

11. A feedstuff in accordance with claim 10, wherein the $1\alpha,24,25$-trihydroxy-vitamin $D_3$ is the 24R-epimer.

12. A feedstuff in accordance with claim 10, wherein the weight ratio of $1\alpha,25$-dihydroxy-vitamin $D_3$ or $1\alpha$-hydroxy-vitamin $D_3$ to $1\alpha,24,25$-trihydroxy-vitamin $D_3$ is about 5:1 to about 1:5.

13. A feedstuff in accordance with claim 12, wherein the weight ratio of $1\alpha,25$-dihydroxy-vitamin $D_3$ or $1\alpha$-hydroxy-vitamin $D_3$ to $1\alpha,24,25$-trihydroxy-vitamin $D_3$ is about 1:1.

14. A method for the treatment of disorders characterized by metabolic calcium and phosphate deficiencies which comprises administering an effective amount of a mixture of hydroxylated derivatives of vitamin D selected from the group consisting of the following mixtures: $1\alpha,25$-dihydroxy-vitamin $D_3$ and $1\alpha,24,25$-trihydroxy-vitamin $D_3$; $1\alpha,25$-dihydroxy-vitamin $D_3$ and $1\alpha,25,26$-trihydroxy-vitamin $D_3$; $1\alpha,25$-dihydroxy-vitamin $D_3$ and $25,26$-dihydroxy-vitamin $D_3$; $1\alpha,25$-dihydroxy-vitamin $D_3$, $24,25$-dihydroxy-vitamin $D_3$, and $1\alpha,24,25$-trihydroxy-vitamin $D_3$; $1\alpha,25$-dihydroxy-vitamin $D_3$, $25,26$-dihydroxy-vitamin $D_3$, and $1\alpha,25,26$-trihydroxy-vitamin $D_3$; $1\alpha$-hydroxy-vitamin $D_3$ and $1\alpha,24,25$-trihydroxy-vitamin $D_3$; and $1\alpha$-hydroxy-vitamin $D_3$ and $1\alpha,25,26$-trihydroxy-vitamin $D_3$.

15. A method in accordance with claim 14, wherein the mixture of hydroxylated derivatives of vitamin D is $1\alpha,25$-dihydroxy-vitamin $D_3$ and $1\alpha,25,26$-trihydroxy-vitamin $D_3$.

16. A method in accordance with claim 14, wherein the mixture of hydroxylated derivatives of vitamin D is selected from the group consisting of the following mixtures $1\alpha,25$-dihydroxy-vitamin $D_3$ and $1\alpha,24,25$-trihydroxy-vitamin $D_3$; and $1\alpha$-hydroxy-vitamin $D_3$ and $1\alpha,24,25$-trihydroxy-vitamin $D_3$.

17. A method in accordance with claim 16, wherein the $1\alpha,24,25$-trihydroxy-vitamin $D_3$ is the 24R-epimer.

18. A method in accordance with claim 16, wherein the weight ratio of $1\alpha,25$-dihydroxy-vitamin $D_3$ or $1\alpha$-hydroxy-vitamin $D_3$ to $1\alpha,24,25$-trihydroxy-vitamin $D_3$ is about 5:1 to about 1:5.

19. A method in accordance with claim 18, wherein the weight ratio of $1\alpha,25$-dihydroxy-vitamin $D_3$ or $1\alpha$-hydroxy-vitamin $D_3$ to $1\alpha,24,25$-trihydroxy-vitamin $D_3$ is about 1:1.

20. A method in accordance with claim 14, comprising administering about 0.05 to about 0.5 μg of each hydroxylated derivative of vitamin D per dosage unit.

21. A pharmaceutical composition in accordance with claim 1, comprising a mixture of hydroxylated derivatives of vitamin D selected from the group consisting of the following mixtures $1\alpha,25$-dihydroxy-vitamin $D_3$ and $1\alpha,25,26$-trihydroxy-vitamin $D_3$; $1\alpha,25$-dihydroxy-vitamin $D_3$ and $25,26$-dihydroxy-vitamin $D_3$; $1\alpha,25$-dihydroxy-vitamin $D_3$ and $24,25$-dihydroxy-vitamin $D_3$ and $1\alpha,24,25$-trihydroxy-vitamin $D_3$; $1\alpha,25$-dihydroxy-vitamin $D_3$ and $25,26$-dihydroxy-vitamin $D_3$ and $1\alpha,25,26$-trihydroxy-vitamin $D_3$; and $1\alpha$-hydroxy-vitamin $D_3$ and $1\alpha,25,26$-trihydroxy-vitamin $D_3$.

22. A feedstuff in accordance with claim 8, comprising a mixture of hydroxylated derivatives of vitamin D selected from the group consisting of the following mixtures $1\alpha,25$-dihydroxy-vitamin $D_3$ and $1\alpha,25,26$-trihydroxy-vitamin $D_3$; $1\alpha,25$-dihydroxy-vitamin $D_3$ and $25,26$-dihydroxy-vitamin $D_3$; $1\alpha,25$-dihydroxy-vitamin $D_3$ and $24,25$-dihydroxy-vitamin $D_3$ and $1\alpha,24,25$-trihydroxy-vitamin $D_3$; $1\alpha,25$-dihydroxy-vitamin $D_3$ and $25,26$-dihydroxy-vitamin $D_3$ and $1\alpha,25,26$-trihydroxy-vitamin $D_3$; and $1\alpha$-hydroxy-vitamin $D_3$ and $1\alpha,25,26$-trihydroxy-vitamin $D_3$.

23. A method in accordance with claim 14, wherein the mixture of hydroxylated derivatives of vitamin D is selected from the group consisting of the following mixtures $1\alpha,25$-dihydroxy-vitamin $D_3$ and $1\alpha,25,26$-trihydroxy-vitamin $D_3$; $1\alpha,25$-dihydroxy-vitamin $D_3$ and $25,26$-dihydroxy-vitamin $D_3$; and $1\alpha,25$-dihydroxy-vitamin $D_3$ and $24,25$-dihydroxy-vitamin $D_3$ and $1\alpha,24,25$-trihydroxy-vitamin $D_3$; $1\alpha,25$-dihydroxy-vitamin $D_3$ and $25,26$-dihydroxy-vitamin $D_3$ and $1\alpha,25,26$-trihydroxy-vitamin $D_3$; and $1\alpha$-hydroxy-vitamin $D_3$ and $1\alpha,25,26$-trihydroxy-vitamin $D_3$.

* * * * *